United States Patent [19]

Brown

[11] Patent Number: 5,063,613
[45] Date of Patent: Nov. 12, 1991.

[54] THUMB PROTECTOR

[76] Inventor: Michael G. Brown, P.O. Box 8249, Houston, Tex. 77387

[21] Appl. No.: 516,820

[22] Filed: Apr. 30, 1990

Related U.S. Application Data

[63] Continuation-in-part of Ser. No. 135,996, Dec. 21, 1987.

[51] Int. Cl.⁵ .................... A61F 5/37; A41D 13/08
[52] U.S. Cl. .................................. 2/21; 128/880
[58] Field of Search ............ 2/16, 161 A, 159, 161 R, 2/158, 160, 163, 162; 128/878, 879, 880, 87 A, 77

[56] References Cited

U.S. PATENT DOCUMENTS

| | | | |
|---|---|---|---|
| D. 170,260 | 8/1953 | Jones | D29/20 |
| 622,386 | 4/1899 | Peery | 2/21 |
| 1,337,957 | 4/1920 | Rasmussen | 2/21 |
| 1,375,690 | 4/1921 | George | 2/21 |
| 1,733,933 | 10/1929 | Beltz | 128/133 |
| 2,232,396 | 2/1941 | Lee et al. | D29/20 |
| 2,389,237 | 11/1945 | Petrullo | D29/20 |
| 2,409,101 | 10/1946 | Brittingham | 2/21 |
| 2,477,126 | 7/1949 | Hartmann | 128/133 |
| 2,536,633 | 1/1951 | Fitch | 128/133 |
| 2,617,413 | 11/1952 | Belknap | 128/133 |
| 3,736,926 | 6/1973 | Irby | 128/133 |
| 3,994,025 | 11/1976 | Petroski | 2/161 |
| 4,051,553 | 10/1977 | Howard | 2/161 |
| 4,062,540 | 12/1977 | Calentine | 2/21 |
| 4,137,572 | 2/1979 | Jansson et al. | 2/16 |
| 4,213,205 | 7/1980 | Smith | 2/161 A |
| 4,287,609 | 9/1981 | Amadeo | 2/16 |
| 4,290,147 | 9/1981 | Bruckner et al. | 2/18 |
| 4,438,532 | 3/1984 | Campanella et al. | 2/16 |
| 4,445,507 | 5/1984 | Eisenberg | 128/133 |
| 4,524,464 | 6/1985 | Primiano | 2/161 A |
| 4,561,122 | 12/1985 | Calentine | 2/21 |
| 4,565,195 | 1/1986 | Eisenberg | 128/133 |
| 4,653,490 | 3/1987 | Eisenberg | 128/133 |
| 4,658,441 | 4/1987 | Smith | 2/161 R |
| 4,709,694 | 12/1987 | O'Connell | 2/167 X |
| 4,787,376 | 11/1988 | Eisenberg | 2/161 A X |

FOREIGN PATENT DOCUMENTS

| | | | |
|---|---|---|---|
| 2588183 | 4/1987 | France | 128/87 A |
| 265598 | 5/1927 | United Kingdom | 128/133 |

Primary Examiner—Werner H. Schroeder
Assistant Examiner—Sara M. Current
Attorney, Agent, or Firm—Kenneth H. Johnson

[57] ABSTRACT

A device to encompass and engage with the thumb to substantially immobilize the metacarpalphalangeal joint, thereby preventing radial deviation of the thumb phalanx while leaving the interphalangeal joint with substantially full flexion.

3 Claims, 2 Drawing Sheets

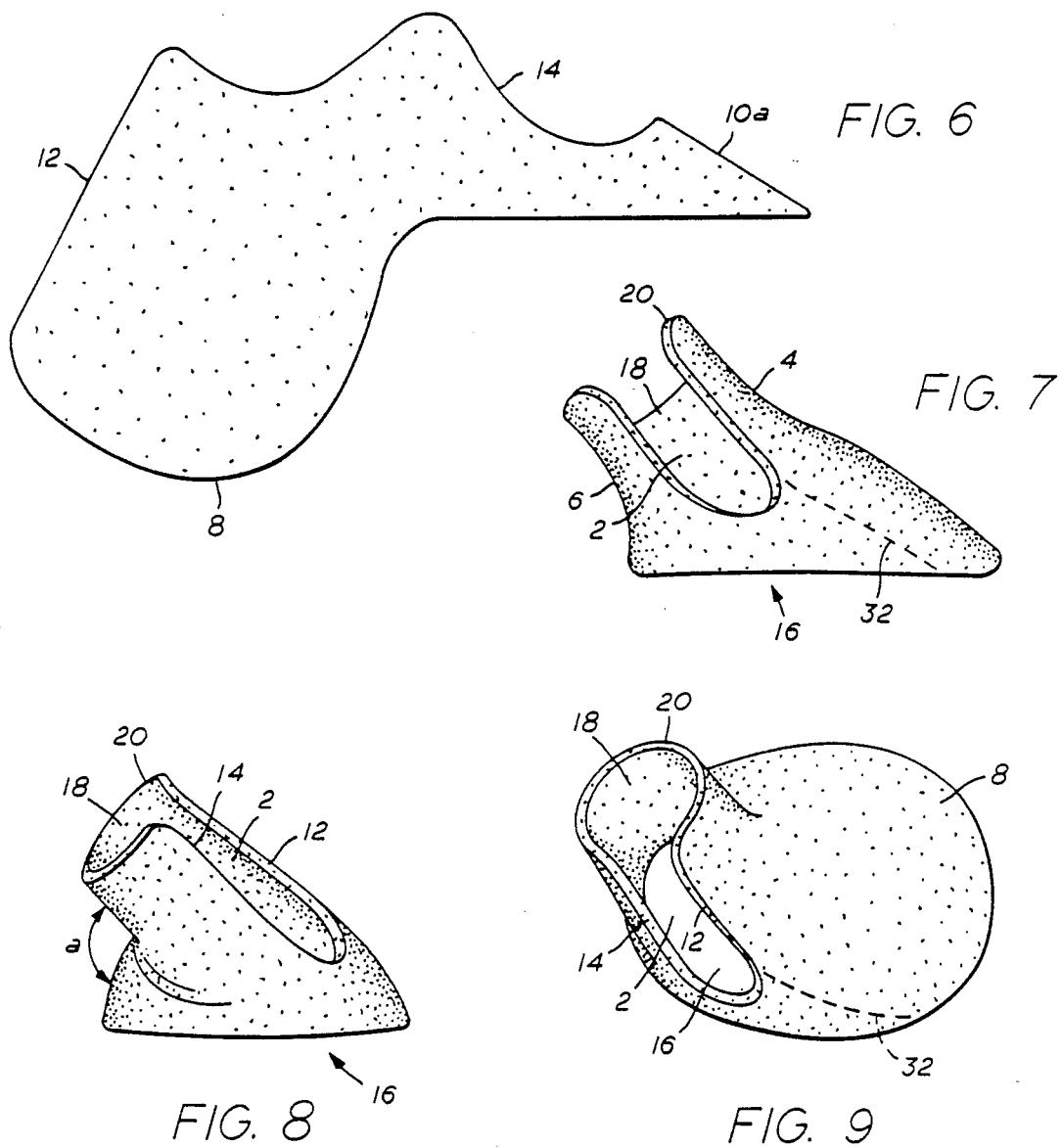

THUMB PROTECTOR

BACKGROUND OF THE INVENTION

This application is a continuation in part of Ser. No. 07/135,996, filed Dec. 21, 1987.

FIELD OF THE INVENTION

The present invention relates to a device which protects the thumb. In particular the present device restricts and preferably prevents radial deviation of the proximal phalanx and rupture of the metacarpalphalangeal (MP) joint ulnar collateral ligament.

RELATED ART

The injury resulting from radial deviation of the proximal phalanx of the thumb is attenuation or rupture of the ulnar collateral ligament. The condition has been commonly called "gamekeepers thumb", which apparently derived from the English gamekeepers method of breaking the neck of a hare which caused great stress to be placed on the ulnar collateral ligaments; and now the term "skier's thumb" is the more frequent term.

Skier's thumb is a common injury which results from a forward fall by the skier which forces the ulnar aspect of the thumb against the planted ski pole. The thumb is pulled into forced abduction and caught between the pole grip and the strap. This places a tremendous force on the structures around the metacarpalphalangeal (MP) joint. The collateral ligament may be either torn or a portion of the proximal phalanx avulsed at the area of its insertion.

This is a very serious injury, which for some professionals can be career ending, such as surgeon, violinist or pianist. The normal corrective treatment would be an immobilizing cast for a minor case, usually for about four weeks, or in the more severe cases where there is a rupture; surgery is indicated. Generally, recovery is less than 100% of the joint mobility prior to the accident.

The number of cases of skier's thumb has been increasing, due possibly to the crowded slopes, less skilled and able skiers and the so-called "hot dog" techniques.

U.S. Pat. No. 4,445,507 to Eisenberg discloses a glove having a retainer (rigid member) disposed radially to the thumb which is intended to restrict the movement of the thumb portion of the glove radially. Additionally, straps going to the fingers are intended to give further stability. This arrangement, however, will not achieve the desired result. When the thumb is stressed as with a ski pole the retainer will tend to slide out of the way of the force and to dig into the hand but the MP joint will still radially deviate.

In U.S. Pat. No. 4,658,441 to Smith, a thumb support made of a flexible sheet of material which straps around the hand and thumb is described. The specific purpose for the device is not given, other than as a thumb support. It would appear to be a splint to provide isolation from the thumb from index finger. The light weight flexible material used would not provide the rigidity necessary to keep the MP joint from opening up under severe stress. Further, there is no rigid three point fixation.

It is an advantage of the present device that it will restrict (prevent in most situations) the radial deviation of the thumb proximal phalanx and the consequent damage to the ulnar collateral ligament of the MP joint. It is a feature of the present invention that although the thumb metacarpalphalangeal joint is restricted in its flexion (i.e. stabilized at a selected functional flexion) the interphalangeal joint retains most of it flexion. Thus, it is an overall advantage of the present invention that the thumb is truly protected, but the functionality of the thumb, in skiing or other activities is substantially retained.

SUMMARY OF THE INVENTION

Briefly the present invention is a device which is slipped onto the user's thumb and held there by its conforming design (conforming to the user's hand). With the exception of the dorsal slot, the device preferably encompasses and covers the area of the thumb described by that portion of hand (including bones and overlying soft tissues) comprising about the distal 80% of the first metacarpal, the thenar eminence, approximately the radial 50% of the first web space, the metacarpalphalangeal joint, and the proximal thumb phalanx up to but not including the condyles of the proximal phalanx. The dorsal slot extends from the distal end of the proximal phalanx past the MP joint. To seat the device on the user's thumb, the dorsal slot is placed over the ulnar surface of the thumb, rotated approximately 90% (ulnar to dorsal to radial) while pressed toward the hand such that the distal end of the device slips proximal to the proximal phalanx condyles at the interphalangeal joint so that the device comes to rest in a position which stabilizes the thumb metacarpalphalangeal joint in slight flexion (about 25°-35°), where it prevents radial deviation of the MP joint and permits full flexion of the interphalangeal joint. The dorsal slot is necessary and allows the device to slip over the user's thumb, rotate and seat in place.

BRIEF DESCRIPTION OF THE DRAWING

FIG. 6 is a plan view of one embodiment of a stock material corresponding to a device as shown in FIGS. 1-9.

FIG. 7 is a front elevational view of the device of FIG. 3

FIG. 8 is a left side elevational view of one embodiment of a device for the left hand.

FIG. 9 is a top plan view of the device of FIG. 8.

DETAILED DESCRIPTION OF THE INVENTION

Figure 1:
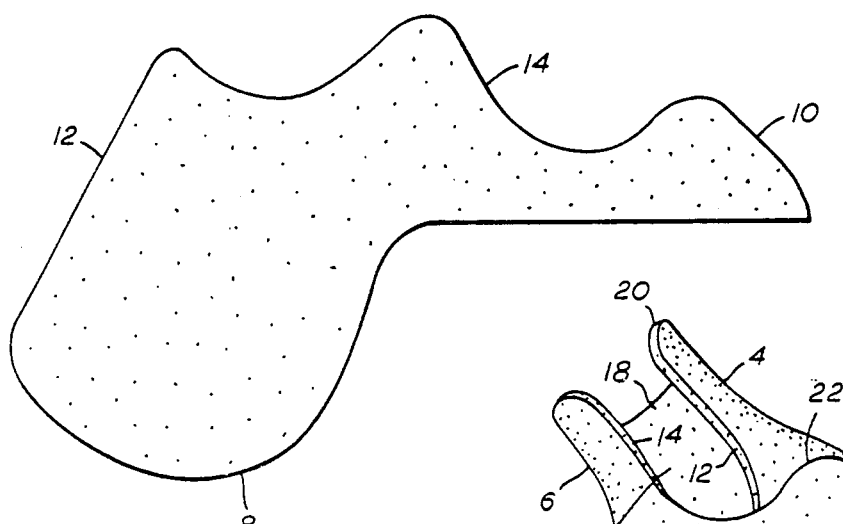
FIG. 1 is a plan view of one embodiment of a stock material corresponding to a device as shown in FIGS. 2-5.
Figure 2:
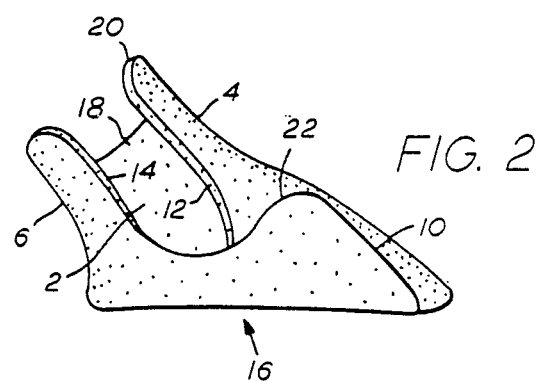
FIG. 2 is a frontal elevational view of the device of FIG. 3.
Figure 3:
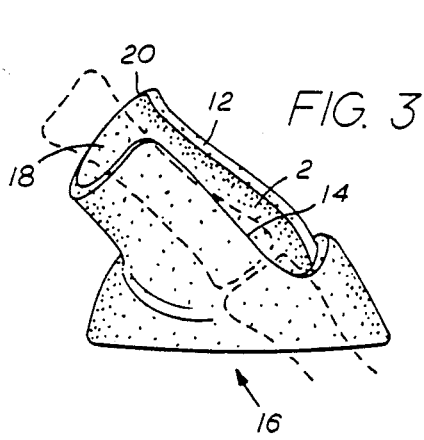
FIG. 3 is a left side elevational view of one embodiment of a device for the left hand.
Figure 4:
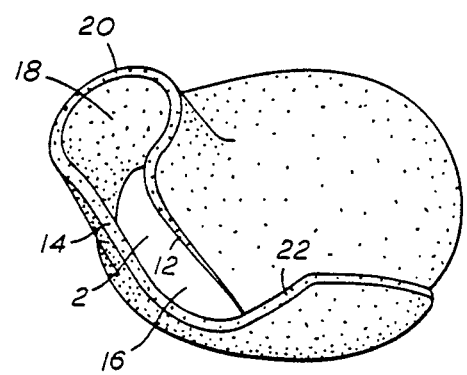
FIG. 4 is a top plan view of the device of FIG. 3
Figure 5:
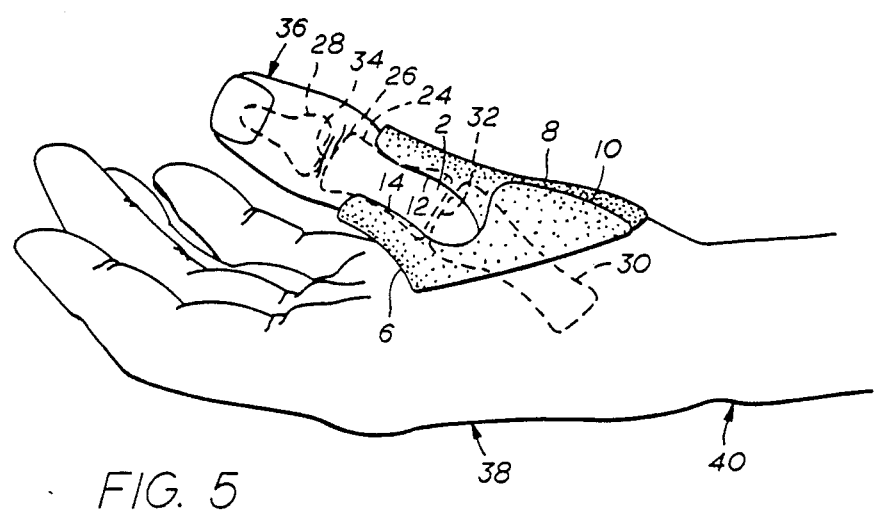
FIG. 5 is a dorsal view of a hand with the device of FIGS. 2-4 in place.

FIGS. 1 and 6 represent two embodiments of blanks useful in one method of fabrication of the present device. Both of these blanks are used when the device is molded on a mold of either standard size hands or of a particular person when the device is custom made. The blank of FIG. 1 related to FIGS. 2-5 is a "global" blank, since it can be used for various size of hands with the terminus 10 being allowed to overlay the middle aspect of the metacarpal radial side 8 of the device. The overlap 22 has no effect on the function or usefulness of the device, but is not aesthetically appealing. The terminus 10 has a rounded, i.e., curved configuration, since it is exposed (generally gloves, will be worn over the hands when the device is used) and shape edges are not desirable. Although the drawings and descriptions are shown for a device for use on the left hand, it should be appreciated that the device for the right is the mirror image and in every way a reversed duplicate of the illustrated device.

The terminus 10a of FIG. 6 related to FIGS. 7-9, is cut so that the terminus 10a does not overlap the middle aspect of the metacarpal radial side 8 of the device, but instead abuts the radial side of the 12 of the dorsal slot 2.

The phantom line 32 shows where the terminus 10a abuts radial slot side 12. If the material used to mold the device is sufficiently softened, e.g., by heating, the juncture 32 may not show.

The present device can also be vacuum formed, extrusion molded, or injection molded in which case the junction 32 will not exist.

It is contemplated that device will be formed of a plastic material. Those formed from the blanks of FIG. 1 and 6 will desirably be thermoplastic, at least at the time the device is fabricated. Plastic materials which crosslink after molding or by exposure to ultraviolet light are useful. However, the plastic material may be thermoplastic, so long as it is rigid under the conditions of use and general under ambient temperature, i.e., up to 130° F. Preferably the device is formed from a material, e.g. plastic, which is sufficient rigid to prevent radial deviation of the thumb at the metacarpalphalangeal joint.

The entire device is rigid. The rigidity which it imparts to the MP joint is what makes it useful. Whatever the method of manufacture used, the device is a rigid structure which surrounds and engages the proximal phalanx portion 24 of a thumb, up to but not including the condyles 26 of the proximal phalanx 24 and having a flared lip 20 about the phalanx opening 18. The flared lip is most pronounced between the radial and ulnar aspect which is the flexion direction of the distal phalanx 28. There is a dorsal slot 2 which prevents any structure of the thumb by the lip 20. The dorsal slot 2 is defined by ulnar side 14 and radial side 12.

The ulnar aspect 6 is smaller than the radial aspect 4 of the device, with the radial aspect 4 extending along and over a portion (about 60-90%) the first metacarpal 30. The rigidity of the device provides a specific predetermined flexion of the metacarpalphalangeal joint 32. The predetermined flexion, angle a is one that corresponds to the natural flexion when the hand is at rest, i.e., about 25° to 35°. However, by terminating the device at the flared lip 20 just below the condyles of the proximal joint, substantial fully flexion of the interphalangeal joint 34 is preserved. The MP joint is 32 substantially immobilized by the device when it is placed on the hand by inserting the thumb 36 through the hand side opening 16. The device is mounted by inserting the thumb 36 through opening 16, with the dorsal slot 2 ulnar and rotating the device ulnar to dorsal to radial aspect 90° while depressing the device toward the hand. This allows that lip to seat below the condyles of the proximate phalanx with the slot being positioned dorsal to the thumb. Rigid three point fixation is provided about the metacarpalphalangeal joint.

The device is generally conformed to the shape of the hand so that it is comfortable to wear for extended periods, on both hands. The extended portion which extends over the first metacarpal provides a brace which shifts any force applied to the thumb to the hand 38 and wrist 40, which are far more massive and generally capable of withstanding the force from the gripped ski poles (not shown) as they push against the ulnar aspect of the device. It is contemplated the device is to be made in different sizes in accordance with the standard ring size of the thumb, which will allow the user to measure the thumb with a ring sizer and select the appropriate sized device (± one ring size).

Although not shown the device may be incorporated in a glove or mitten.

The invention claimed is:

1. A thumb protector characterized as a rigid structure conformed to fit a human hand and adapted to removably engage and surround a portion of a thumb of a human hand comprising:
   (a) an ulnar portion having a predetermined acute angle therein and adapted to extend continuously about the ulnar aspect of the proximal phalanx of the thumb and to extend to a predetermined terminus adjacent to the interphalangeal joint of said thumb and
   (b) a radial portion continuous with said ulnar portion and adapted to extend about a portion of the radial aspect of said thumb and to extend to a predetermined terminus adjacent to the interphalangeal joint of said thumb; said ulnar portion and said radial portion being separated by a dorsal slot and flared about said terminus thereby providing a specified fixed flexion of the metacarpalphalangeal joint, substantially full flexion of the interphalangeal joint and inhibiting radial deviation of the thumb at the metacarpalphalangeal joint by three point fixation whereby the user is protected against rupture of the thumb metacarpalphalangeal joint ulnar collateral ligament.

2. The thumb protector according to claim 1 wherein said angle corresponds to the natural flexion of the metacarpalphalangeal joint.

3. The thumb protector according to claim 2 wherein said angle is about 25° to 35°.

4. The thumb protector according to claim 1 wherein the ulnar portion is smaller than the radial portion.

5. The thumb protector according to claim 4 wherein said radial portion is adapted to extent over a major portion of the first metacarpal of a hand when in place.

6. The thumb protector according to claim 5 wherein said radial portion extends over 60 to 90% of a metacarpal of a hand when in place.

7. The thumb protector according to claim 1 wherein said terminus is continuous from said ulnar portion through said radial portion.

8. The thumb protector according to claim 7 wherein said flare is greatest in an area between said ulnar and radial portions.

* * * * *